(12) United States Patent
Kitching et al.

(10) Patent No.: US 11,819,377 B2
(45) Date of Patent: *Nov. 21, 2023

(54) GENERATING 3D MODELS OF A PATIENT'S TEETH BASED ON 2D TEETH IMAGES

(71) Applicant: Align Technology, Inc., San Jose, CA (US)

(72) Inventors: Ian Kitching, Saratoga, CA (US); Ka M. Cheang, Sunnyvale, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,455

(22) Filed: Jan. 23, 2023

(65) Prior Publication Data
US 2023/0157789 A1    May 25, 2023

Related U.S. Application Data

(60) Continuation of application No. 16/852,251, filed on Apr. 17, 2020, which is a continuation of application No. 14/952,642, filed on Nov. 25, 2015, now Pat. No. 10,624,716, which is a division of application No. 14/152,776, filed on Jan. 10, 2014, now Pat. No. 9,364,297, which is a continuation of application No. 13/293,916, filed on Nov. 10, 2011, now Pat. No. 8,636,510, which is a continuation of application No. 11/760,612, filed on Jun. 8, 2007, now Pat. No. 8,075,306.

(51) Int. Cl.
*A61C 7/00* (2006.01)
*G16H 50/50* (2018.01)
*G16Z 99/00* (2019.01)

(52) U.S. Cl.
CPC ............... *A61C 7/002* (2013.01); *A61C 7/00* (2013.01); *G16H 50/50* (2018.01); *G16Z 99/00* (2019.02)

(58) Field of Classification Search
CPC .................................. A61C 7/002; A61C 7/08
See application file for complete search history.

(56) References Cited

U.S. PATENT DOCUMENTS

| | | | |
|---|---|---|---|
| 6,227,850 B1 | 5/2001 | Chishti et al. | |
| 6,227,851 B1 | 5/2001 | Chishti et al. | |
| 6,299,440 B1 | 10/2001 | Phan et al. | |
| 6,318,994 B1 | 11/2001 | Chishti et al. | |
| | (Continued) | | |

FOREIGN PATENT DOCUMENTS

WO    WO-2006065955 A2 *    6/2006    ........... A61B 5/1111

*Primary Examiner* — Ralph A Lewis
(74) *Attorney, Agent, or Firm* — Shay Glenn LLP

(57) ABSTRACT

Methods for obtaining an adjusted 3D model of patient's teeth based on a 2D image of the patient's teeth. In some examples, the method includes: obtaining a 3D digital model based on a scan of the patient's teeth; obtaining a 2D image based on a camera picture; iteratively comparing a distance between corresponding points on one or more teeth of the 3D digital model and of the 2D image, and generating an adjusted 3D model in which the one or more teeth of the 3D digital model are moved to reduce said distance, wherein iteratively comparing and generating comprises iterating until one or more deviations between the teeth of the 3D digital model and the 2D image are below a threshold.

26 Claims, 12 Drawing Sheets

(56) References Cited

U.S. PATENT DOCUMENTS

| | | |
|---|---|---|
| 6,386,878 B1 | 5/2002 | Pavlovskaia et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,739,869 B1 | 5/2004 | Taub et al. |
| 6,767,208 B2 | 7/2004 | Kaza |
| 7,040,896 B2 | 5/2006 | Pavlovskaia et al. |
| 7,063,532 B1 | 6/2006 | Jones et al. |
| 7,074,039 B2 | 7/2006 | Kopelman et al. |
| 7,108,508 B2 | 9/2006 | Hedge et al. |
| 7,134,874 B2 | 11/2006 | Chishti et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 8,038,444 B2 | 10/2011 | Kitching et al. |
| 8,044,954 B2 | 10/2011 | Kitching et al. |
| 8,075,306 B2 * | 12/2011 | Kitching ............... A61C 7/00 382/128 |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,636,510 B2 * | 1/2014 | Kitching ............... A61C 7/002 382/128 |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,364,297 B2 * | 6/2016 | Kitching ............... G16H 50/50 |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,624,716 B2 * | 4/2020 | Kitching ............... A61C 7/00 |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,154,381 B2 | 10/2021 | Roschin et al. |
| 11,259,896 B2 | 3/2022 | Matov et al. |
| 11,357,598 B2 | 6/2022 | Cramer |
| 11,395,717 B2 | 7/2022 | Yuryev et al. |
| 11,432,908 B2 | 9/2022 | Kopelman et al. |
| 11,464,604 B2 | 10/2022 | Makarenkova et al. |
| 11,478,334 B2 | 10/2022 | Matov et al. |
| 11,484,389 B2 | 11/2022 | Sterental et al. |
| 11,521,732 B2 | 12/2022 | Levin et al. |
| 11,534,272 B2 | 12/2022 | Li et al. |
| 11,553,988 B2 | 1/2023 | Mednikov et al. |
| 11,633,268 B2 | 4/2023 | Moalem et al. |
| 11,642,195 B2 | 5/2023 | Gao et al. |
| 11,651,494 B2 | 5/2023 | Comito et al. |
| 11,654,001 B2 | 5/2023 | Roschin et al. |
| 2003/0008259 A1 | 1/2003 | Kuo et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0048432 A1 * | 3/2005 | Choi ............... A61C 7/002 433/24 |
| 2005/0182654 A1 | 8/2005 | Abolfathi et al. |
| 2005/0244791 A1 | 11/2005 | Davis et al. |
| 2006/0079981 A1 * | 4/2006 | Rubbert ............... A61C 7/146 700/98 |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2016/0310235 A1 | 10/2016 | Derakhshan et al. |
| 2017/0273760 A1 | 9/2017 | Morton et al. |
| 2018/0280118 A1 | 10/2018 | Cramer |
| 2019/0328487 A1 | 10/2019 | Levin et al. |
| 2019/0328488 A1 | 10/2019 | Levin et al. |
| 2020/0155274 A1 | 5/2020 | Pimenov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2021/0134436 A1 | 5/2021 | Meyer et al. |
| 2021/0174477 A1 | 6/2021 | Shi et al. |

\* cited by examiner

Matching Assistant

The following are teeth that have not been matched:

| Tooth ID | Distance... | Match Status |
|---|---|---|
| 4 | 0.0694 | Inspect for mis-match collision |
| 6 | 0.0960 | fluctuation |
| 7 | 0.0831 | fluctuation |
| 17 | 0.0738 | fluctuation |
| 19 | 0.0676 | inspect for mis-match collision |
| 20 | 0.0739 | fluctuation |
| 25 | 0.0655 | inspect for mis-match collision |
| 32 | 0.0728 | fluctuation |

Advance Properties

Tooth 4-6: Collision statistics mismatch. Was 0.2969mm (now 0.0906mm). Please inspect matching tooth against the impression to make sure that matching is correct.

Average matching distance  0.0694  mm

Please Lower starting distance to be within 0.30mm.

☐ Trim colliding teeth automatically?

[Re-match] [Done]

FIG. 11

Question

⚠ The following teeth are over the acceptable matching surface limit (0.100mm):
([0.1500mm] for last Molar)
   Tooth 23  0.1501
   Tooth 24  0.1557
   Tooth 25  0.1318
   Tooth 26  0.1346

Please go back and rematch them! Teeth not match within limit might create unfitted Aligners.
Click YES to go back and rematch.

[Yes]   [No] — 86

FIG. 15

GENERATING 3D MODELS OF A PATIENT'S TEETH BASED ON 2D TEETH IMAGES

CROSS-REFERENCE

This application is a continuation of U.S. patent application Ser. No. 16/852,251, filed Apr. 17, 2020, now U.S. Patent Application Publication No. 2020/0237477, which is a continuation of U.S. patent application Ser. No. 14/952,642, filed Nov. 25, 2015, now U.S. Pat. No. 10,624,716, which is a divisional of U.S. patent application Ser. No. 14/152,776, filed Jan. 10, 2014, now U.S. Pat. No. 9,364,297, which is a continuation of U.S. patent application Ser. No. 13/293,916, filed Nov. 10, 2011, now U.S. Pat. No. 8,636,510, which is a continuation of U.S. patent application Ser. No. 11/760,612, filed Jun. 8, 2007, now U.S. Pat. No. 8,075,306, the contents of which are hereby incorporated by reference in their entirety.

FIELD OF THE INVENTION

This invention relates to the field of orthodontics, and more particularly to a system and method for detecting deviations from a planned course of treatment to gradually reposition teeth.

BACKGROUND OF THE INVENTION

A fundamental objective in orthodontics is to realign or reposition a patient's teeth to positions where the teeth function optimally and aesthetically. Methods have been developed to reposition a patient's teeth to a prescribed tooth arrangement (i.e. a desired final arrangement of each tooth in a patient's jaw) according to a planned course of treatment using a series of appliances. The series of incremental position adjustment appliances are placed over the patient's teeth and gradually reposition the teeth. Each appliance represents a pre-existing stage in a series of pre-existing stages for repositioning teeth to a prescribed final position. This is described in U.S. Pat. No. 5,975,893; which is assigned to the assignee of the present application, and the complete disclosures of which is incorporated herein by reference.

Ideally, a patient wears each appliance for about two weeks or until the pressure of each appliance on the teeth can no longer be felt. At that point, the patient replaces a current adjustment appliance with a next adjustment appliance in the series until no more appliances remain. During treatment, a patient may forget to wear the appliances regularly allowing the patient to stray from the prescribed course. As a result, one or more appliances may not properly fit and the dentist (or any other medical professional) may have to start the process again ("re-start") by taking another impression of the patient's teeth so that a new series of incremental position adjustment appliances can be electronically generated and ultimately manufactured to a new prescribed tooth arrangement.

When a re-start occurs, there is an opportunity to track what progress has occurred to straighten the patient's teeth. To accurately track the progress of a patient's teeth, it is desirable to have an exact model of the patient's teeth for comparison.

Conventional methods provide process steps for creating generalized record keeping for images of a patient's teeth by moving standard teeth in a standard three-dimensional (3D) digital model template to reflect the general position of a patient's teeth. Since the size and shape of any tooth of the standard 3D model may vary from actual teeth of the patient, the images may only provide a visual likeness and not an exact tooth structure or position to allow for accurate tracking of tooth movement or fabrication of adjustment appliances, such as aligners, which use actual teeth geometry.

In conventional methods, a patient's X-ray image is displayed on a computer screen as a background image for the standard 3D model. The standard 3D model is then rotated, translated and scaled by a technician to match the orientation of the X-ray image. Then the individual teeth are adjusted to match those in the X-ray. However, the model generated by conventional methods is not an exact model of the patient's teeth but merely an approximate model of the patient's teeth because instead of actual patient teeth, standard teeth are used. Hence, the patient's progress cannot be accurately tracked and reliable data is unavailable to manufacture adjustment appliances.

Therefore, a system and method for detecting deviations from a prescribed course of treatment to gradually reposition teeth to a pre-existing prescribed tooth arrangement; and accurately tracking the progress of a patient's teeth are needed.

SUMMARY OF THE INVENTION

In one embodiment, a method for detecting and correcting deviation during an orthodontic treatment plan is provided. The method includes the steps of receiving an un-segmented current teeth image representing a patient's teeth after an orthodontic treatment plan has begun and before the plan ends for the patient; matching a previously segmented teeth model with the current teeth image; and generating at least one corrective stage to define an intermediate tooth arrangement, wherein the at least one corrective stage repositions a digital teeth image so that a prescribed tooth arrangement of the previously segmented teeth model can be used.

This brief summary has been provided so that the nature of the disclosure may be understood quickly. A more complete understanding of the disclosure can be obtained by reference to the following detailed description of the various embodiments thereof in connection with the attached drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The foregoing features and other features of the present disclosure will now described with reference to the drawings of the various embodiments. In the drawings, the same components have the same reference numerals. The illustrated embodiments are intended to illustrate, but not to limit the disclosure. The drawings include the following Figures:

FIG. 11 is a screen shot of a dialog box for displaying the teeth with a matching error greater than pre-determined parameters, according to one embodiment of the present disclosure;

FIG. 15 is a screen shot of a message warning the technician that at least one tooth is over the acceptable matching surface limit, according to one embodiment of the present disclosure.

DETAILED DESCRIPTION OF THE INVENTION

Figure 1:
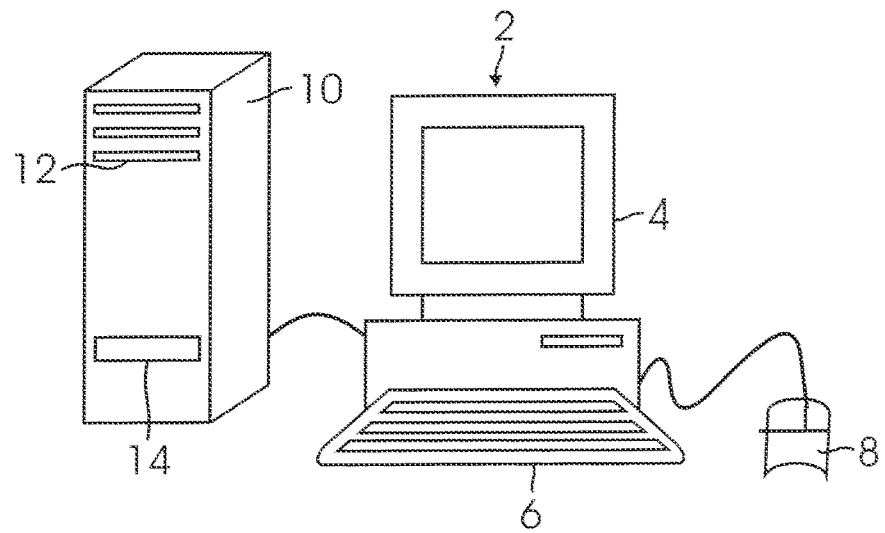
FIG. 1 shows a block diagram of a computing system for executing process steps, according to one embodiment of the present disclosure.

The following definitions are provided as they are typically (but not exclusively) used in the computing and orthodontics environment, implementing the various embodiments disclosed herein.

"Corrected Stages" means creating new stages from a Previously Segmented Teeth Model(s) stage by causing the teeth in the Previously Segmented Teeth Model to move from a Current Teeth Image to the same position in a pre-existing Prescribed Tooth Arrangement or one of the pre-existing stages of a Previously Segmented Teeth Model so that the Prescribed Tooth Arrangement established by the Previously Segmented Teeth Model can be used and will not change. Before any new Corrected Stages can be digitally created, a stage of the Previously Segmented Teeth Model for the patient captured by the Current Teeth Image is selected and then adjusted to match the Current Teeth Image. In one embodiment, a pre-existing stage corresponds to a previous appliance worn by the patient or an appliance that was intended to be worn at some time after the previous appliance was worn, but before the Prescribed Tooth Arrangement. By correcting the patient's teeth to the pre-existing Prescribed Tooth Arrangement, a set of new appliance are provided to the patient, although a last appliance will provide the same Prescribed Tooth Arrangement as initially provided. By correcting the patient's teeth to a pre-existing stage, the Prescribed Tooth Arrangement will not change and any pre-existing appliances may be used, which saves time and money to digitally create and physically manufacture new appliances or a new prescribed tooth arrangement.

"Current Teeth Image" means a digital image (two dimensional or three dimensional) representing a patient's teeth at any time after beginning treatment but prior to the teeth being in a Prescribed Tooth Arrangement. The image can be taken from a dental impression, a 2D image (such as a camera picture) and a bite registry, multiple 2D images, intra-oral scan of low or high resolution, X-ray, cone scan, CT-scan, and other methods. The Current Teeth Image may be a digital model but may not be segmented, which is a labor intensive process step. The Current Teeth Image should provide or enable, by software, a certain level of clarity of the teeth so that a Previously Segmented Teeth Model can be adjusted to match the Current Teeth Image.

"Digital Data Set" means any information that may be used to represent a patient's teeth arrangement. This information may be acquired in a plurality of ways, for example (a) by scanning dental impressions which are typically received from a dental laboratory; (b) a patient's teeth may be scanned or imaged using X-Rays, cone scan, computer aided tomographic images; (c) scanning digital pictures of a patient's teeth; (d) scanning and digitizing analog pictures; (e) or any other method.

"Initial Segmented Teeth Model" means the Initial Segmented Teeth Model that is created at the beginning of a patient's treatment plan.

"Prescribed Tooth Arrangement" means an arrangement of a patients teeth at the end of a treatment plan, created from an Initial Segmented Teeth Model.

"Previously Segmented Teeth Model" means a digital 3D segmented model that provides specific incremental stages of segmented teeth arrangement to move teeth from the Initial Segmented Teeth Model to the Prescribed Tooth Arrangement. The Previously Segmented Teeth Model is created before the Current Teeth Image is available. By comparing a Previously Segmented Teeth Model to the initial Corrected Stage, a patient's progress during an orthodontic treatment plan can be tracked and any deviation from the desired treatment path can be detected by a technician well before a doctor or a patient could recognize the deviation or understand that it could hinder or prevent the most effective and efficient Prescribed Tooth Arrangement.

"Segmented Teeth Model" means a digital 3D model that has been segmented so that each tooth may be represented as a separate digital object. The segmentation step is performed by software and is labor intensive.

"Teeth Model" means a digital 3D model incorporating dental information associated with a patient's teeth. Typically, the model is based on the Digital Data Set.

In one embodiment, the present disclosure provides a system and method for detecting deviations from a prescribed course of treatment to gradually reposition teeth. When a patient's orthodontic treatment begins a Segmented Teeth Model is generated and used to create a set of stages (e.g., pre-existing stages) from the Initial Segmented Teeth Model to the Prescribed Tooth Arrangement. From the set of pre-existing stages, a set of incremental adjustment appliances are created to move the patient's teeth into a prescribed tooth arrangement. However, a patient's teeth may stray from the planned course of treatment. This can be as a result of unforeseen physical traits of a patient's teeth or prolonged periods of non-use of the appliances by the patient, or some other reason. As a result, one or more appliances will have a geometry that is inoperative or uncomfortable to wear by the patient. To correct these deviations, which may occur at any stage of treatment a Corrected Stage or stages are created which will position the patient's teeth to conform to a pre-existing stage or the pre-existing Prescribed Tooth Arrangement. New appliances are generated from the corrected stage or stages. If the generated appliances manufactured from the Corrected Stages do not bring the patient's teeth directly to the pre-existing Prescribed Tooth Arrangement, they will bring the patient's teeth back in the position of a pre-existing stage so that the already created appliances can continue to be used to move the patient's teeth into the Prescribed Tooth Arrangement.

There are a number of reasons why the Corrected Stages may move the teeth directly to the pre-existing Prescribed Tooth Arrangement, thereby avoiding the use of pre-existing appliances made from the Previously Segmented Teeth Model. For example, the Current Teeth Image may present some new treatment difficulties that cannot be effectively and efficiently resolved by the remaining pre-existing appliances, so a new set of appliance will need to be created from the Corrected Stages to reach the Prescribed Tooth Arrangement. On the other hand, logistically, from a distribution aspect, it may be easier and less confusing to send the doctor a new complete set of appliances from the Corrected Stages than to ask the doctor or patient to integrate a few new appliances from the Corrected Stages into the pre-existing appliances from the Previously Segmented Teeth Model.

The system can be implemented in software and executed by a computing system. To facilitate an understanding of the preferred embodiment. the general architecture and operation of a computing system will be described first. The specific process under the preferred embodiment will then be described with reference to the general architecture.

FIG. 1 is a block diagram of a computing system for executing computer executable process steps according to one embodiment of the present disclosure. FIG. 1 includes a host computer 2 and a monitor 4. Monitor 4 may be a CRT, a LCD, a plasma, or any other type of color or monochrome display. Also provided with computer 2 are a keyboard 6 for entering data and user commands, and a pointing device (for example, a mouse) 8 for processing objects displayed on monitor 4.

Computer 2 includes a computer-readable memory storage device 10 for storing readable data. Besides other programs, storage device 10 can store application programs including web browsers and computer executable code, according to the present disclosure. According to one embodiment of the present disclosure, computer 2 can also access computer-readable removable storage devices storing data files, application program files, and computer executable process steps embodying the present disclosure or the like via a removable memory device 12 (for example, a CD-ROM, CD-R/W, flash memory device, zip drives, floppy drives and others).

It is noteworthy that the present disclosure is not limited to the FIG. 1 architecture. For example, notebook or laptop computers, or any other system capable of connecting to a network and running computer-executable process steps, as described below, may be used to implement the various aspects of the present disclosure.

Figure 2:
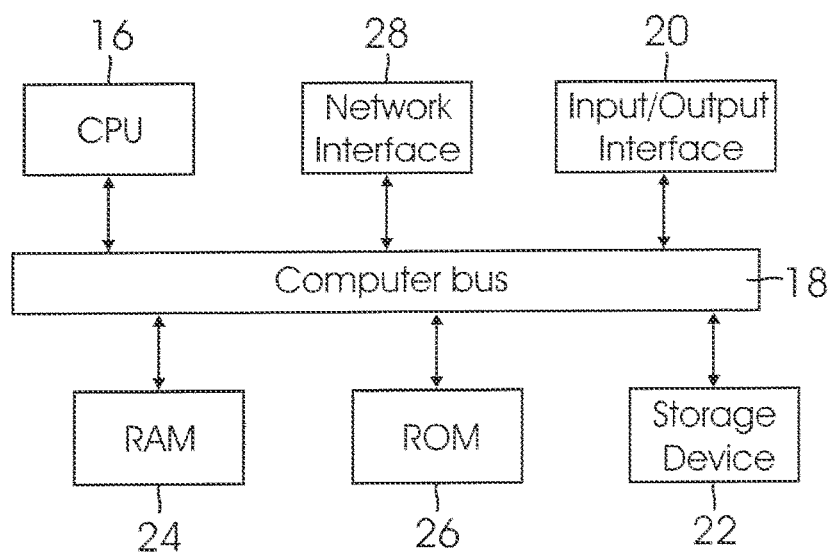
FIG. 2 shows the internal architecture of the computing system of FIG. 1.

FIG. 2 shows a top-level block diagram showing the internal functional architecture of computing system 2 that may be used to execute the computer-executable process steps, according to one embodiment of the present disclosure. As shown in FIG. 2, computing system 2 includes a central processing unit (CPU) 16 for executing computer-executable process steps and interfaces with a computer bus 18.

Also shown in FIG. 2 are an input/output interface 20 that operatively connects output display devices such as monitors 4, input devices such as keyboards 6 and a pointing device such as a mouse 8.

A storage device 22 (similar to device 10) also interfaces with computing system 2 via computer bus 18. Storage device 22 may be disks, tapes, drums, integrated circuits, or the like, operative to hold data by any means, including magnetically, electrically, optically, and the like. Storage device 22 stores operating system program files, application program files, computer-executable process steps of the present disclosure, web-browsers and other files. Some of these files are stored on storage device 22 using an installation program. For example, CPU 16 executes computer-executable process steps of an installation program so that CPU 16 can properly execute the application program.

Random access memory ("RAM") 24 also interfaces with computer bus 18 to provide CPU 16 with access to memory storage. When executing stored computer-executable process steps from storage device 22, CPU 16 stores and executes the process steps out of RAM 24.

Read only memory ("ROM") 26 is provided to store invariant instruction sequences such as start-up instruction sequences or basic input/output operating system (BIOS) sequences.

Computing system 2 can be connected to other computing systems through a network interface 28 using computer bus 18 and a network connection (for example 14). Network interface 28 may be adapted to one or more of a wide variety of networks, including local area networks, storage area networks, wide area networks, the Internet, and the like.

In one embodiment of the disclosure, course correction software may be supplied on a CD-ROM or a floppy disk or alternatively could be read from the network via network interface 28. In yet another embodiment of the disclosure, computing system 2 can load the course correction software from other computer readable media such as magnetic tape, a ROM, integrated circuit, or a magneto-optical disk.

Alternatively, the course correction software is installed onto the storage device 22 of computing system 2 using an installation program and is executed using the CPU 16.

In yet another aspect, the course correction software may be implemented by using an Application Specific Integrated Circuit that interfaces with computing system 2.

Figure 3:
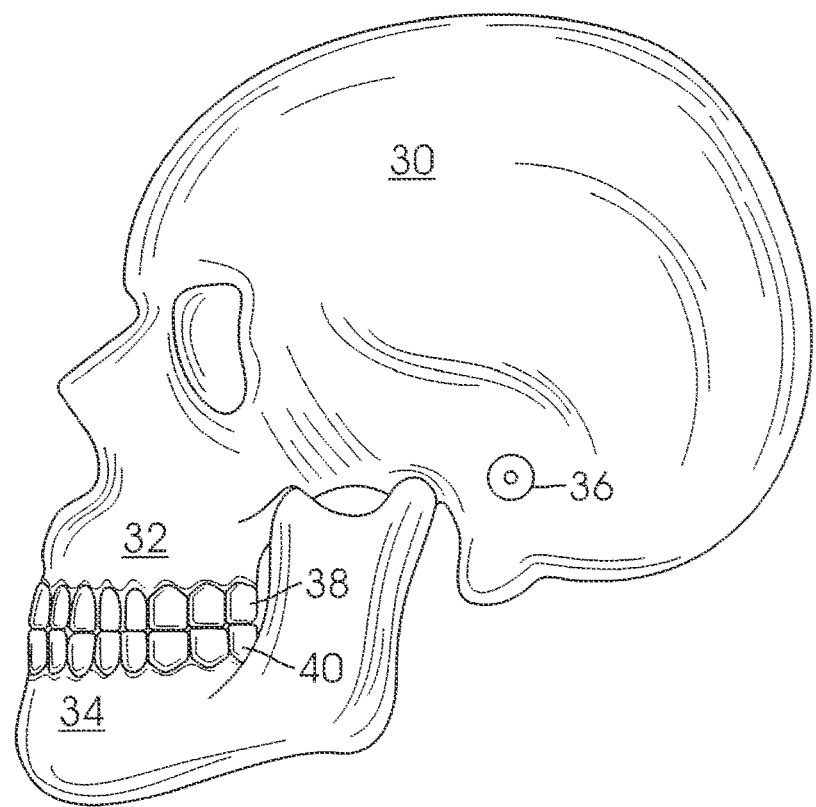
FIG. 3 is an elevational diagram showing the anatomical relationship of the jaws of a patient.

Turning to FIG. 3, a skull 30 with an upper jaw bone 32 and a lower jaw bone 34 is shown. Lower jaw bone 34 hinges at a joint 36 to skull 30. Joint 36 is called a temporal mandibular joint (TMJ). Upper jaw bone 32 is associated with an upper jaw 38, while lower jaw bone 34 is associated with a lower jaw 40.

A computer model of jaws 38 and 40 is generated, and a computer simulation models interactions among the teeth on jaws 38 and 40. The computer simulation allows the system to focus on motions involving contacts between teeth mounted on the jaws and to render realistic jaw movements that are physically correct when jaws 38 and 40 contact each other. The model of the jaw places the individual teeth in a treated position. Further, the model can be used to simulate jaw movements including protrusive motions, lateral motions, and "tooth guided" motions where the path of lower jaw 40 is guided by teeth contacts rather than by anatomical limits of jaws 38 and 40. Motions are applied to one jaw, but may also be applied to both jaws. Based on the occlusion determination, the prescribed tooth arrangement can be ascertained.

Figure 4A:
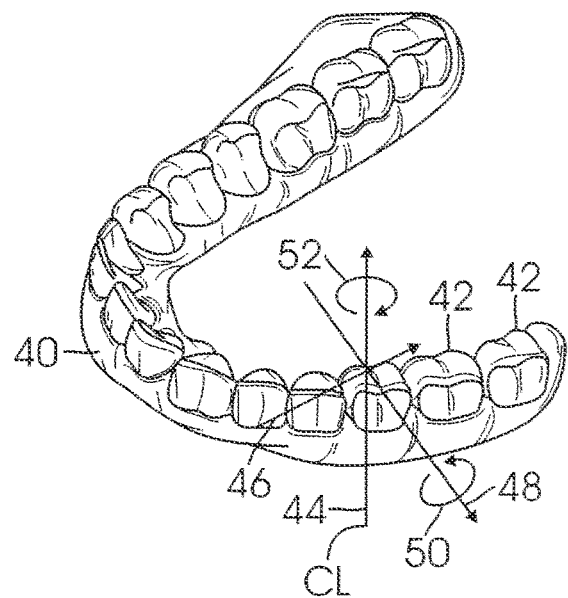
FIG. 4A illustrates in more detail the patient's lower jaw and provides a general indication of how teeth may be moved by the methods and system of the present disclosure.

Referring now to FIG. 4A, lower jaw 40 includes a plurality of teeth 42, for example. At least some of these teeth may be moved from a Previously Segmented Teeth Models to a prescribed tooth arrangement. As a frame of reference describing how a tooth may be moved, an arbitrary centerline (CL) may be drawn through tooth 42. With reference to this centerline (CL), each tooth may be moved in orthogonal directions represented by axes 44, 46, and 48 (where 44 is the centerline). The centerline may be rotated about axis 48 (root angulation) and axis 44 (torque) as indicated by arrows 50 and 52, respectively. Additionally, tooth 42 may be rotated about the centerline, as represented by arrow 52. Thus, all possible free-form motions of the tooth can be performed.

Figure 4B:
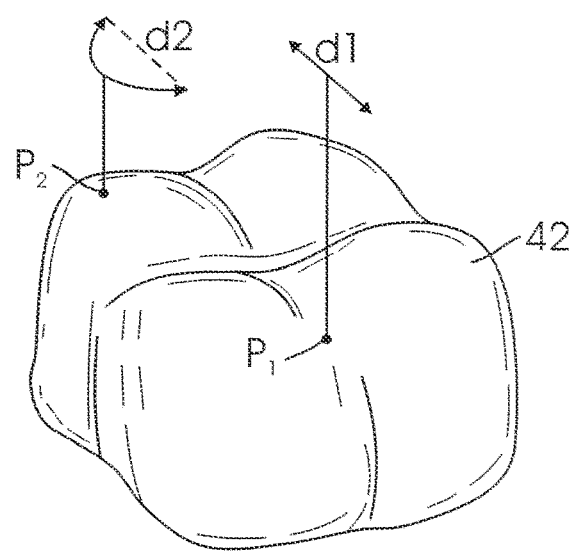
FIG. 4B illustrates a single tooth from FIG. 4A and defines how tooth movement distances are determined.

FIG. 4B shows how the magnitude of any tooth movement may be defined in terms of a maximum linear translation of any point P on tooth 42. Each point P will undergo a cumulative translation as tooth 42 is moved in any of the orthogonal or rotational directions defined in FIG. 4A. That is, while point P will usually follow a nonlinear path, there is a linear distance between any point P in the tooth when determined at any two times during the treatment. Thus, an arbitrary point P1 may in fact undergo a true side-to-side translation as indicated by arrow d1. while a second arbitration point P2 may travel along an arcuate path, resulting in a final translation d2. Many aspects of the present disclosure are defined in terms of the maximum permissible movement of point P1 induced on any particular tooth. Such maximum tooth movement, in turn, is defined as the maximum linear translation of point P1 on the tooth that undergoes the maximum movement for tooth 42 in any treatment step.

Figure 5:
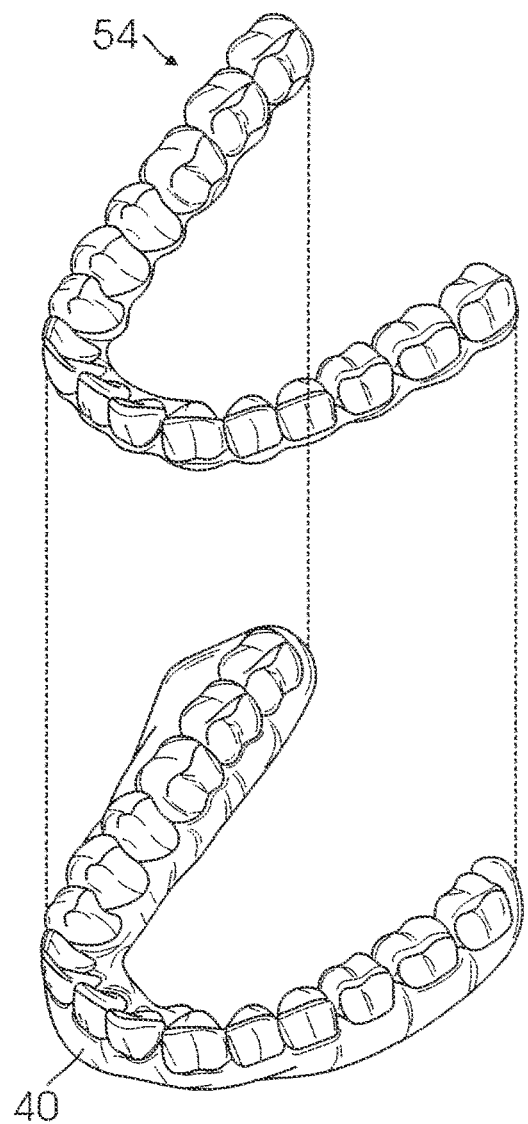
FIG. 5 illustrates the jaw of FIG. 4A together with an incremental position adjustment appliance.

FIG. 5 shows one adjustment appliance 54 which is worn by the patient in order to achieve an incremental repositioning of individual teeth in the jaw as described generally above. Appliance 54 is a polymeric shell having a teeth-receiving cavity. This is described in U.S. Pat. No. 6,450,807, which claims priority from U.S. Pat. No. 5,975,893, which in turn claims priority from provisional application Ser. No. 06/050,352, filed Jun. 20, 1997 (collectively the "prior applications"); all of which are assigned to the assignee of the present application, and the disclosures of which are incorporated herein by reference in their entireties.

As set forth in the prior applications, each polymeric shell may be configured so that its tooth-receiving cavity has a geometry corresponding to a pre-existing stage intended for appliance 54. The patient's teeth are repositioned to a prescribed tooth arrangement by placing a series of incremental position adjustment appliances over the patient's teeth. The adjustment appliances are generated at the beginning of the treatment from pre-existing stages generated from an impression taken of the patient's teeth. Ideally, the patient wears each appliance for two weeks or until the pressure of each appliance on the teeth is minimal. At that point, the patient moves onto the next stage of the planned course of treatment and replaces the current adjustment appliance with the next adjustment appliance in the series until no more appliances remain. Conveniently, the appliances are generally not affixed to the teeth and the patient may place and replace the appliances at any time during the procedure.

The polymeric shell 54 can fit over all teeth present in the upper or lower jaw. Typically, only certain one(s) of the teeth will be repositioned while others of the teeth will provide a base or an anchor region for holding appliance 54 in place as appliance 54 applies a resilient repositioning force against the tooth or teeth to be repositioned. In complex cases, however, multiple teeth may be repositioned at some point during the treatment. In such cases, the moved teeth can also serve as a base or anchor region for holding the repositioning appliance.

Polymeric appliance 54 of FIG. 5 may be formed from a thin sheet of a suitable elastomeric polymer, such as Tru-Tain 0.03, in thermal forming dental material, available from Tru-Tain Plastics, Rochester, Minn. Typically, no wires or other means will be provided for holding the appliance in place over the teeth. In some cases, however, it will be desirable or necessary to provide individual anchors on teeth with corresponding receptacles or apertures in appliance 54 so that the appliance can apply an upward force on the tooth that would not be possible in the absence of such an anchor.

As discussed above, a patient's teeth may stray from the planned course of treatment. This can be as a result of unforeseen physical traits of a patient's teeth, prolonged periods of non-use of the appliances by the patient or other reasons. As a result, one or more appliances will have a geometry that is undesirable or unable to effectively move teeth to a desired position or stage. Without the system and method of the present disclosure, the dentist would have to start the repositioning process again by taking another impression of the patient's teeth.

The new impression for the re-start process captures the patient's new initial or current position so that a new 3D digital model of the teeth can be created, each tooth defined and segmented, the gingival line formed, and all stages created to effectively move the teeth from a current position to a new prescribed tooth arrangement. The prescribed tooth arrangement is new during a re-start case because the new stages created during this process are never matched to a pre-existing stage or the pre-existing prescribed tooth arrangement, but instead create new stages to reach a new, yet similar, prescribed tooth arrangement. This is described in U.S. Pat. No. 7,077,647, which is assigned to the assignee of the present application, and the complete disclosure of which is incorporated herein by reference.

In contrast, the system and method of the present disclosure allows for adjustment of any teeth that are off track from any of the pre-existing stages to a Corrected Stage(s) to reach the pre-existing Prescribed Tooth Arrangement or a pre-existing stage of the Previously Segmented Teeth Model. The corrected stage or stages are used to create the additional appliances.

Figure 6:
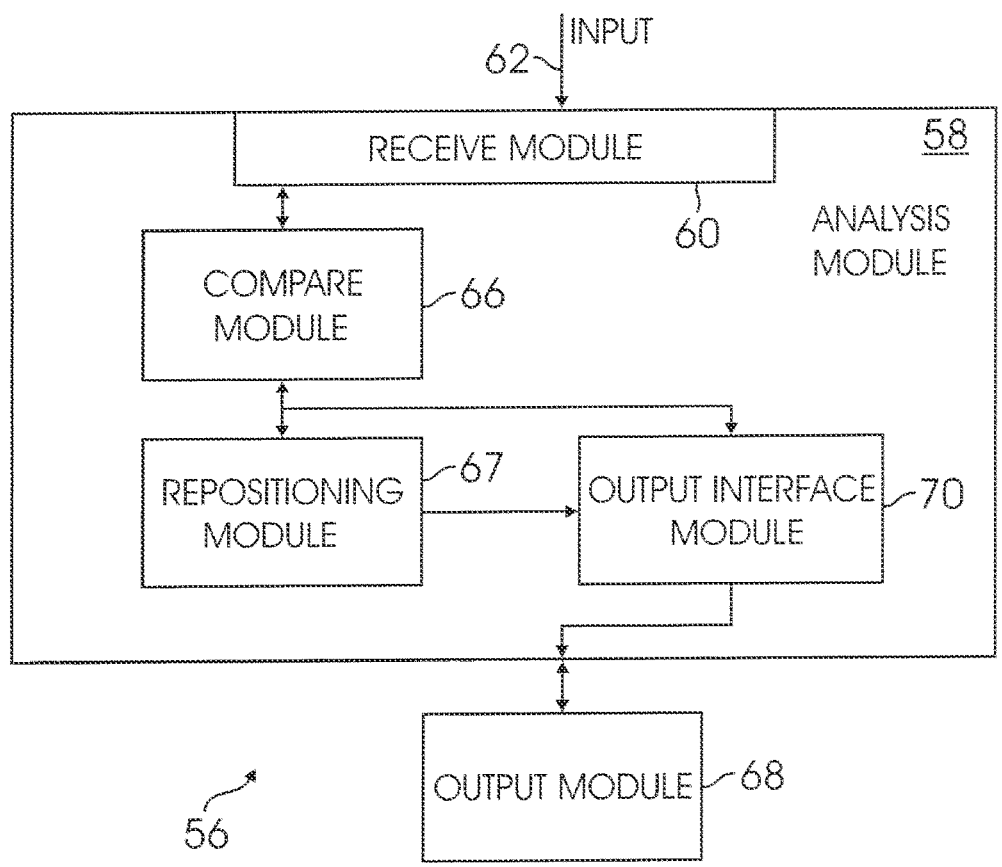
FIG. 6 shows a block diagram of a system for correcting deviations during the prescribed course of an orthodontic treatment to gradually reposition teeth, according to one embodiment of the present disclosure.

FIG. 6 shows a block diagram of a system 56 for correcting deviations from a planned orthodontic treatment course to gradually reposition teeth, according to one embodiment of the present disclosure. System 56 comprises an analysis module 58 having a receive module 60 for receiving input data 62. Input data 62 includes (1) Current Teeth Image; and (2) Previously Segmented Teeth Model.

A technician obtains a Previously Segmented Teeth Model or an Initial Segmented Teeth Model that was created from the initial impression of the patient's teeth taken at the beginning of the orthodontic treatment. The technician can use any stage of the Previously Segmented Teeth Model. For tracking purposes and analysis to correct similar deviations in the future, the technician will typically use the stage of the Previously Segmented Teeth Model that is most closely related to the Current Teeth Image. In other words, the stage Previously Segmented Teeth Model for the last appliance worn or next to be worn is likely to be used.

The Current Teeth Image may be generated from an impression of the patient's teeth, a 2D image (such as a camera picture) and a bite registry. multiple 2D images, intraoral scan of low or high resolution, X-ray, CT-scan and others taken during the course of the treatment. A technician pre-processes the Current Teeth Image, prior to being input into receive module 6 by manually assigning a unique Facial Axis of the Clinical Crown (FACC), a unique current identifier (e.g., abnormalities in a tooth or attachments or markers placed on a tooth), or by using a cusp or surface matching algorithm, to each tooth. Each tooth in the Previously Segmented Teeth Model is already assigned a unique starting identifier like FACC.

A compare module 66, within analysis module 58, compares the Current teeth Image with the Previously Segmented Teeth Model to determine if there is an initial match. To determine if there is an initial match, the Current teeth Image with the Previously Segmented Teeth Model are overlaid on each other and the relative location of each tooth is identified by its unique identifier or FACC. If no mismatches are generated, an initial match occurs. The initial match confirms that the technician is using the correct Previously Segmented Teeth Model for the Current Teeth Image.

A mismatch occurs if there are any teeth numbering irregularities, for example, the total number of teeth in each model is not the same, or at least one tooth is missing a FACC.

A technician reviews mismatch details and corrects the mismatch (es) by manually adjusting or repositioning each tooth with a mismatch using the Previously Segmented Teeth Model or adjusting information relating to each tooth with a mismatch, as described below. By knowing a current location of each tooth, the difference between the current location and a previous location can be measured and tracked to understand the adjustments made and possibly how to prevent a similar deviation in the future. In addition, based on this distance, the technician uses the Previously Segmented Teeth Model to move or reposition each tooth with a mismatch from its present location to a desired location.

When the technician adjusts the Previously Segmented Teeth Model, the adjustment data is input into receive module 60 and sent to repositioning module 67 which receives the data via compare module 66. Repositioning module 67 uses this data to reposition the teeth with mismatches. When the mismatches have been corrected, the corrected stages are transmitted back to compare module 66 and the process is repeated until an initial match is achieved. The initial match provides a good starting position for the next step in the process, matching the surfaces of the corresponding teeth.

After an initial match is achieved, compare module 66 executes a surface matching algorithm which prompts the technician to enter bite match settings. Bite match settings include pre-determined tolerances and the number of times a surface matching algorithm can be executed, as described below with reference to FIG. 10. Any tooth from the Previously Segmented Teeth Model that is found to be within a pre-set tolerance away from the starting position is a good surface match and the tooth is repositioned accordingly.

The surface matching algorithm takes a number of samples of each tooth in the Previously Segmented Teeth Model and finds the closest corresponding sampling point on the jaw image in the Current Teeth Image. A grid is created on each tooth and the number of samples is randomly selected and then the grid is overlaid on the Current Teeth Image. This is done as the Current Teeth Image needs to match the Previously Segmented Teeth Model. If the match is off by a millimeter, when repositioned to match the data, the tooth is also off by a millimeter. This process is done iteratively until the deviations are below a certain threshold of the overall point data set differences.

Repositioning module 67 allows a technician to utilize a Previously Segmented Teeth Model of the patient's teeth to reposition each tooth that has a mismatch or deviation above pre-determined tolerances. Thus, a technician does not need to go through the laborious process of creating a segmented tooth model for the Current Teeth Image. Consequently, the Current Teeth image may be a lesser quality image or format as long as the resolution is high enough to allow the matching process.

When repositioning is completed, the Corrected Stages are communicated to an output module 68 via an output interface module 70 within analysis module 58. Output module 68 may be any device with a monitor or any device capable of receiving a communication.

It is noteworthy that analysis module 58 may be implemented in software code or by using application specific integrated circuits (ASIC). The present adaptive aspects are not limited to the modular structure shown in FIG. 6, more or fewer components may be used to implement module 58.

Figure 7:
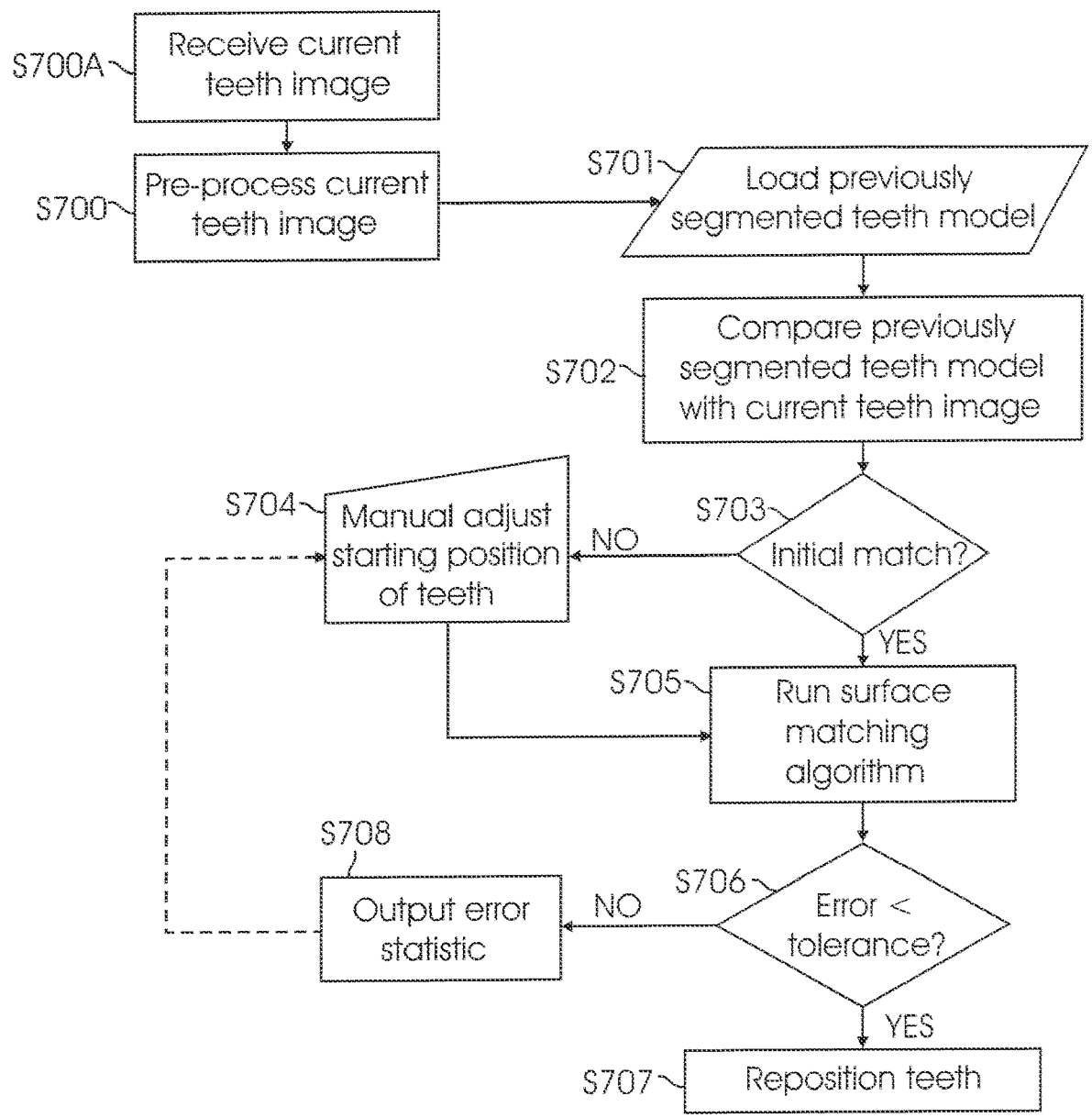
FIG. 7 is a flow chart showing the steps of correcting deviations during a prescribed course of treatment to gradually reposition teeth, according to one embodiment of the present disclosure.

FIG. 7 is a flow chart showing the steps of detecting deviations from a planned course of treatment to gradually reposition teeth, according to one embodiment of the present disclosure. The process starts in step S700A, when a Current Teeth Image is received or obtained by a technician.

In step S700, the Current Teeth Image is pre-processed using a digital data software tool and each tooth is assigned a Facial Axis of the Clinical Crown (FACC), i.e. a unique current identifier, with jaw characteristics set. In one embodiment, the Current Teeth Image does not need to be segmented, which saves a technician's time and hence reduces overall cost for processing digital teeth data.

In step S701, a Previously Segmented Teeth Model is selected, and is input into system 56 of FIG. 6 with the Current Teeth Image. Depending on the stage, the Previously Segmented Teeth Model may be the Initially Segmented Teeth Model, the Prescribed Tooth Arrangement or some stage there between.

In step S702, the Previously Segmented Teeth Model and the Current Teeth Image are compared. An initial matching algorithm is executed which matches the unique starting identifiers (FACCs) of each tooth in the Previously Segmented Teeth Model to the respective unique current identifiers (FACCs) of each tooth in the Current Teeth Image as assigned in step S700. The images are overlaid on each other and the relative location of each tooth is identified by its unique identifier (or FACC) to determine if there are any mismatches in step S703. The initial matching process is performed to determine if there is a gross mismatch so that a technician does not waste time in performing surface matching (step S705) that is described below.

If any mismatches are found, an initial match has not occurred and the mismatches are displayed in the form of an informational dialog that provides details of the mismatches, such as teeth numbering irregularities or missing FACCs. A mismatch occurs if there are any teeth numbering irregularities, for example, the total number of teeth in each model is not the same, or at least one tooth is missing a FACC.

In step S704, a technician manually adjusts or repositions each tooth with a mismatch using the Previously Segmented Teeth Model or adjusts the information relating to each tooth with a mismatch. By knowing a current location of each tooth, the distance between the current location from a starting location can be measured. Based upon this distance, the technician uses the Previously Segmented Teeth Models to move or reposition each tooth with a mismatch from its present location to the desired location creating corrected stages. Thereafter, the process moves to step S705 that is described below.

If no mismatches are generated in step S703, then an initial match occurs and the process moves to step S705. The initial match confirms that the technician is using the correct Previously Segmented Teeth Model and the Current Teeth Image, which provides a good starting point for executing a surface matching algorithm. It is noteworthy that although the process steps S702 (initial matching) and S705 (surface matching) are shown as separate steps, they may be performed in a single step.

In step S705, system 56 (see FIG. 6) executes a surface matching algorithm. The surface matching algorithm takes a number of samples of each tooth in the Previously Segmented Teeth Model and finds the closest corresponding sampling point on the Current Teeth Image. A grid is created on each tooth and the number of samples is randomly selected and then the grid is overlaid on the Current Teeth Image.

In step S706, any resulting errors from the surface matching algorithm are compared to predetermined tolerances (as described below with reference to FIG. 10) to determine if the resulting errors are less than the predetermined tolerance. If the resulting errors are less than the pre-determined tolerance, then in step S707, the teeth in the Previously Segmented Teeth Model are repositioned corresponding to a corrected stage.

If the resulting errors are greater than the pre-determined tolerance, then in step S708, error statistics for the surface matching algorithm is output to a display device. The display provides suggestions to perform certain steps to get a better match. In some cases, a technician may manually adjust the teeth that did not match in step S706. After the manual adjustment, the process moves back to step S705 and the surface matching algorithm is re-run.

It is noteworthy that although it is convenient to perform the initial matching step, a technician may choose to perform only the surface matching step and based on the results manually adjust the teeth and then re-run the surface matching step.

It is noteworthy that the adaptive aspects disclosed herein allows one to track the adjustments made to each tooth of the Previously Segmented Tooth model to match the Current Teeth Image. Furthermore, one can create Corrective Stages with the Previously Segmented Teeth model from a tooth arrangement of a Current Teeth Image to a Prescribed Tooth Arrangement or a Previously Segmented Teeth model.

Figure 8:
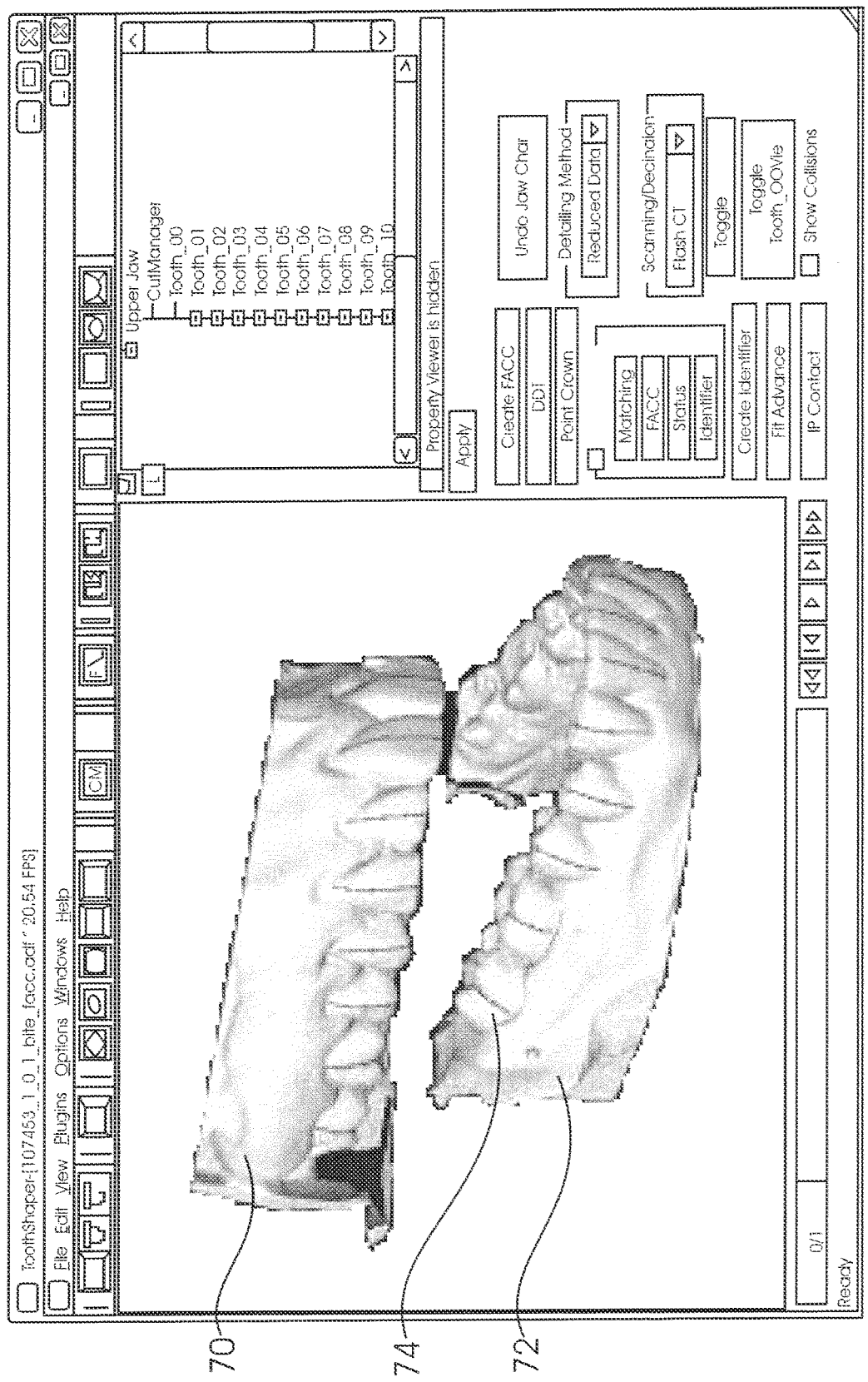
FIG. 8 is a screen shot showing a graphical representation of a three-dimensional model of a patient's upper and lower jaws based on a current digital data set, according to one embodiment of the present disclosure.

FIG. 8 is a screen shot showing a graphical representation of a three-dimensional model of a patient's upper and lower jaws 70, 72 generated from a Current Teeth Image. As described above, using a digital detailing tool (DDT), a technician pre-processes the Current Teeth Image by assigning and placing FACC's or unique current identifiers 74 on each tooth in the model. Unique current identifiers are landmarks on the teeth for the purposes of matching which include attachments or specific characteristics of a tooth. Each FACC has a number associated with it and that is the tooth number, so the same tooth from the Previously Segmented Teeth Models and the Current Teeth Image should be in a similar location.

Figure 9:
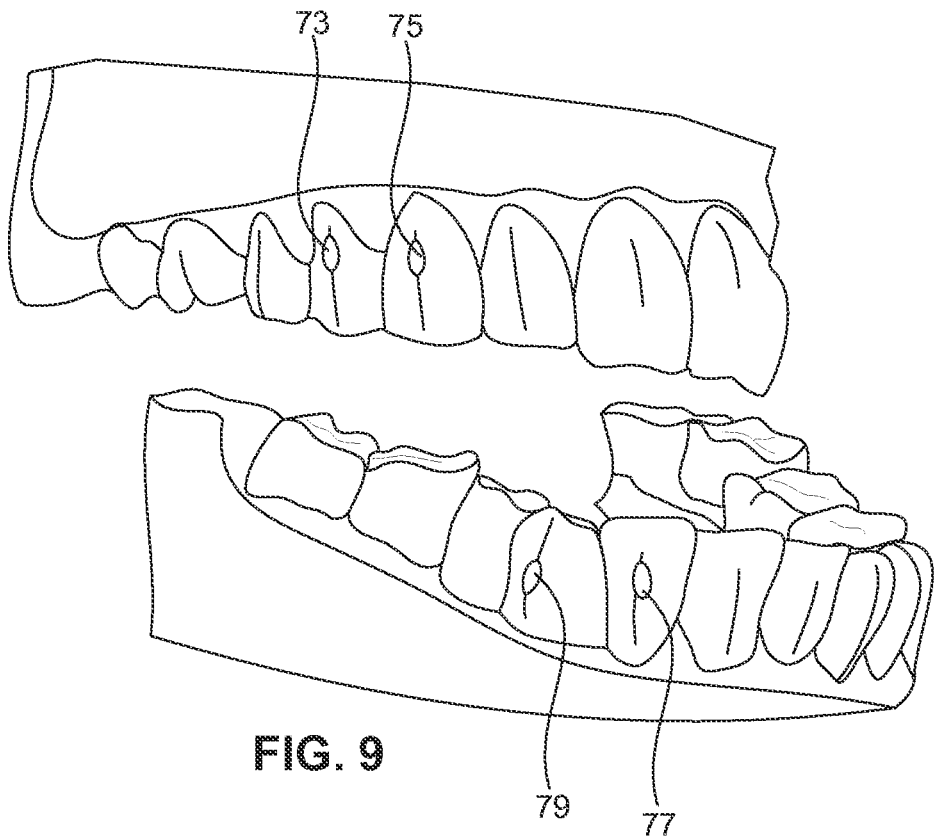
FIG. 9 is a graphical representation of a three-dimensional model of an initial match that can occur when the three dimensional model of digital translated images are overlaid on three dimensional model of the Current Teeth Image. according to one embodiment of the present disclosure.

FIG. 9 is a graphical representation of a three-dimensional model of an initial match (step S703, FIG. 7) that may occur when a Previously Segmented Teeth Model is overlaid on the Current Teeth Image, according to one embodiment of the present disclosure. The initial match provides a starting position for subsequent surface matching so that a good match is achieved.

If the initial matching algorithm determines that one or more teeth are mismatched, the initial matching algorithm cannot complete the initial matching satisfactorily because of teeth numbering irregularities or missing FACCs. In this instance, the initial matching algorithm will generate an informational dialog giving details of the mismatches allowing the technician to correct them and execute the initial matching algorithm again. Also shown in FIG. 9 are four attachments 73, 75, 77, 79 that have been added to four of the patient's teeth. An attachment assists to anchor an appliance to a tooth, assist in moving a tooth to a desired position or correct imperfections in a tooth, such as uneven surfaces, so that the appliances will fit properly.

Figure 10:
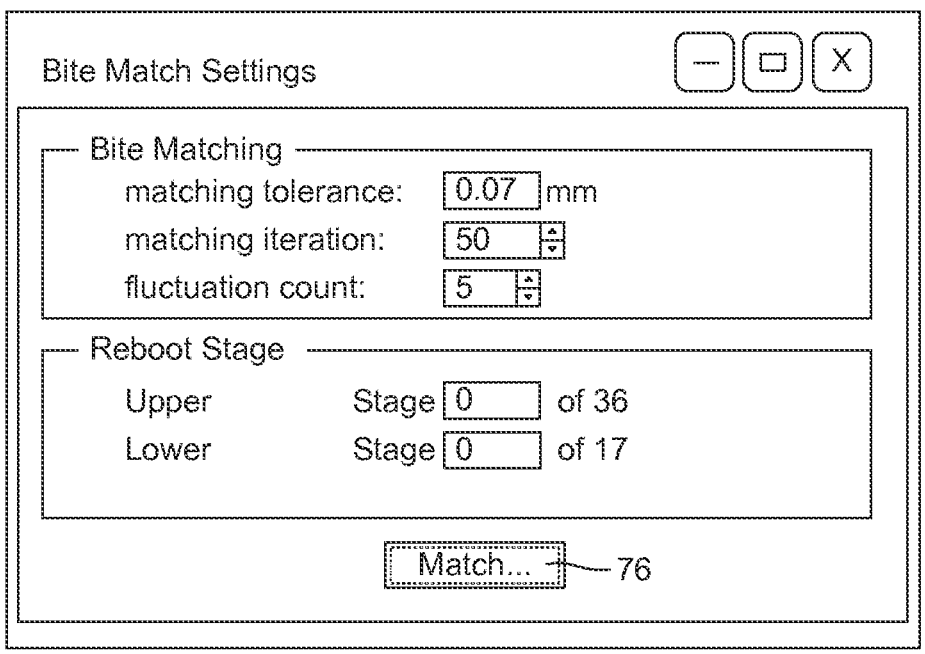
FIG. 10 is a screen shot of a menu for entering bite match settings, according to one embodiment of the present disclosure.

FIG. 10 is a screen shot of a menu for entering bite match settings, according to one embodiment of the present disclosure for performing the surface matching process step S705 (FIG. 7). Upon selecting the surface matching algorithm, a menu for entering bite match settings is displayed prompting the technician to enter the bite matching settings. The bite matching settings are pre-determined parameters or tolerances. The pre-determined tolerances include (1) a matching tolerance which defines when the tooth and the Current Teeth Image surfaces qualify as a match; (2) a maximum iteration which is the number of matching iteration steps that the algorithm is allowed to run; (3) a fluctuation count which defines the number of steps allowed before the algorithm is stopped as an error is not reduced (sometimes the matching algorithm runs into a local surface matching minimum and can not minimize further to achieve the tolerance as the starting positioning is not good enough, or there is a discrepancy between the Previously Segmented Teeth Model and the Current Teeth Image); and (4) reboot stage information is taken from the RX (or original planned course of treatment as determined by an orthodontist) and used for two types of course correction, reboot and refinement.

With reboot, the patient has not completed treatment, but the appliances no longer fits. Each stage in the reboot represents an appliance in the series of appliances. The technician enters the stage for both the upper and lower teeth where the teeth have strayed from the planned course of treatment.

With refinement, the patient has completed the planned course of treatment, but the teeth were not repositioned as expected. In other words, the patient has used all the appliances but the teeth still require repositioning requiring the patient to start from the beginning of the process.

Once the technician has entered the pre-determined tolerances, the technician selects a match button 76 causing the surface matching algorithm to be executed (step S705, FIG. 7). During this process each tooth in the Previously Segmented Teeth Model is matched with the corresponding tooth in the Current Teeth Image. If a tooth from the Previously Segmented Teeth Model is found to be within a pre-set tolerance away from the Current Teeth Image, it determined (or concluded) that a good match is found and the program positions the tooth to this new matching transform to create a corrected set of stages.

When the matching operation is complete the results are displayed in an interactive dialog box (or user-interface) (81), as shown in the screen shot of FIG. 11. Dialog box 81 includes a top segment 81A that displays teeth which were not matched. A user can select a particular tooth, for example, tooth number 4 (shown in dotted rectangle 81B). This generates a report on the selected tooth. The report is shown as segment 81C and labeled as Advanced Properties.

The report identifies the error type (for example, "Collision statistics mismatch. Was 0.2969 mm (now 0.0906 mm); the distance a tooth needs to move to create a good match and a suggestion on how to correct the error. Suggestions are generated by using a current matching distance and the type of error status (for example, "collision statistics mismatch") for each tooth. For example, segment 81C shows the average matching distance to be 0.0694 and the software interface tells the technician to lower the distance to be within 0.030 mm. The technician can reposition the mismatched teeth (step S704) and select the "re-match" option (shown by box 82). This re-runs the surface matching algorithm.

Dialog box 81 also includes a "Trim colliding teeth automatically" checkbox 80, which allows the technician to indicate if a corrected bite (for example, stage 0 in one of the corrected stages) includes any stripped teeth as the starting (un-stripped) teeth. If the stripped teeth are matched, they can cause severe hard collisions. Selecting option 80 automatically trims colliding teeth.

When the matching is complete and matching errors for each tooth are below the parameters defined by the technician, each tooth from the Previously Segmented Teeth Model are translated and rotated to create a corrected stage. The teeth are repositioned in stages, where each appliance in the series of appliances represents a stage. Upon completion of the surface matching program, the corrected stage with an overlay of the corrected stages is displayed to provide visual feedback on the accuracy of the matching. After all the teeth have been matched, or when the technician decides the match is good enough, the technician selects done button 78 causing the Previously Segmented Teeth Models to be automatically deleted.

When no match is found, the matching program is terminated when either the maximum fluctuation count is reached or the maximum iteration is reached. Upon termination, a dialog box is generated identifying the teeth with a matching error greater than the pre-determined tolerances.

As described above, the surface matching algorithm takes a number of samples of the Previously Segmented Teeth Model and finds the closest corresponding sampling point on the jaw image in the Current Teeth Image. A grid is created on each tooth and the number of samples is randomly selected and then the grid is overlaid on Current Teeth Image. This is done as the Current Teeth Image needs to match the Previously Segmented Teeth Model. This process is done iteratively until the deviations are below a certain threshold of the overall point data set differences.

The surface matching algorithm takes each grid and randomly selects, points and superimposes them. The number of points selected is the number of data points that are to be measured. Once all the points have been selected and measured, they are superimposed onto the starting teeth setting and if all the differences on average are below a threshold set by the technician (for example 0.07 mm). then there is a close match.

Both the Previously Segmented Teeth Model and the Current Teeth Image have different frames of reference, so in some cases it is possible to not get a good match. Different frames of reference can occur as a result of lost enamel, a chipped tooth or a bad impression (air bubble).

When the surface matching algorithm is executed, the parts or teeth that did not get a good match are displayed. When there are mismatches, the technician then manually repositions the teeth in the Previously Segmented Teeth Model (step 5704, FIG. 7) and re-runs the initial matching algorithm for the teeth with the errors. (The Current Teeth Image cannot be moved as it is merely a mesh of data.) After re-running the initial matching algorithm, any mismatches (or errors) are displayed and technician evaluates whether or not the errors are acceptable.

Figure 12:
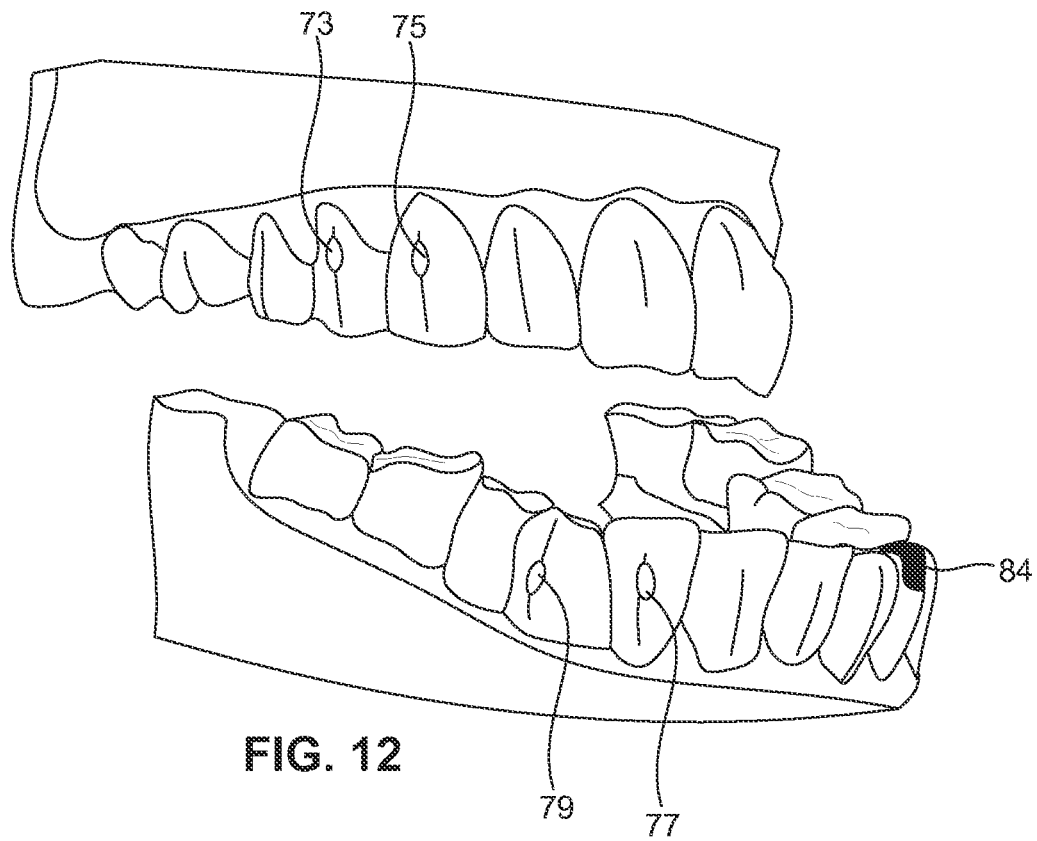
FIG. 12 is a graphical representation of a three-dimensional model of a patient's upper and lower jaw with a matching error, according to one embodiment of the present disclosure.

FIG. 12 is a graphical representation of a three-dimensional model of the patient's upper and lower jaw with a matching error, according to one embodiment of the present disclosure. The teeth with matching errors are marked 84 for easy identification.

Figure 13:
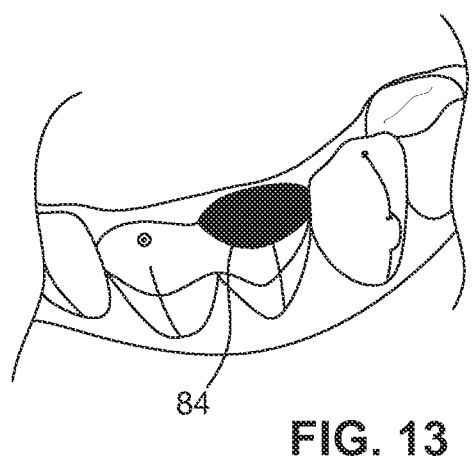
FIG. 13 is an enlarged view of a portion of the jaw in FIG. 12 showing the matching error to be corrected.

A better starting positioning for the matching algorithm needs to be obtained for the teeth identified in the dialog box 81 (FIG. 11). To obtain a better starting positioning, the technician manually adjusts each tooth marked 84 from the Previously Segmented Teeth Model to the desired location on the corrected stages. FIG. 13 is a screen shot of an enlarged view of a portion of the jaw in FIG. 12 showing matching error 84.

Figure 14:
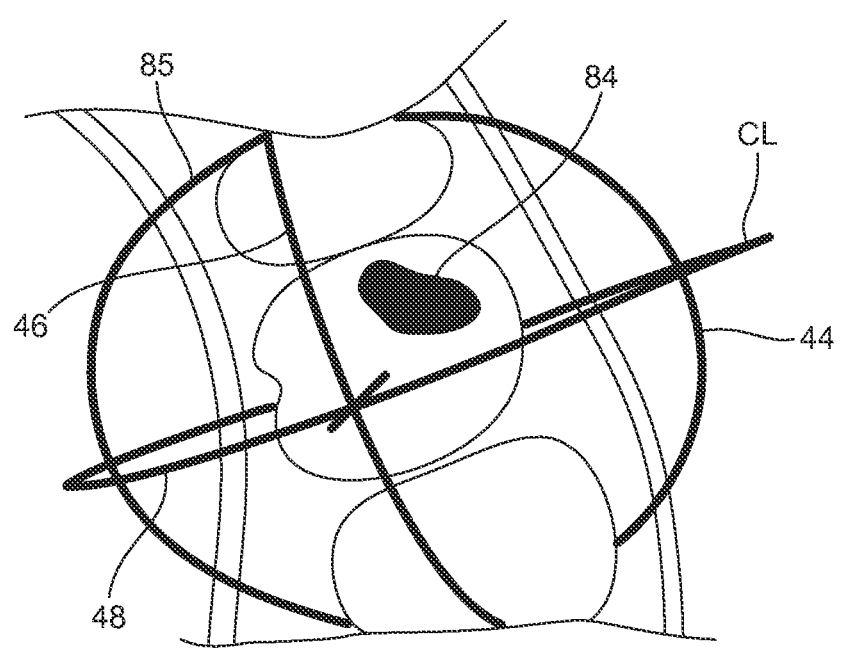
FIG. 14 is an enlarged top view of a portion of the jaw in FIG. 12 showing the matching error to be corrected.

FIG. 14 is an enlarged top view of a portion of the jaw in FIG. 12 showing the matching error 84. As described with reference to FIG. 4, a tooth is re-positioned by drawing an arbitrary centerline CL through the tooth to be re-positioned. With reference to centerline (CL), tooth 84 may be moved in orthogonal directions represented by axes 44, 46, and 48. The centerline may be rotated about axis 48 (root angulation) and axis 44 (torque). Additionally, the tooth may be rotated about the centerline allowing all possible free-form motions of tooth 84 to be performed. A guidance box 85 is placed over the tooth 84 with matching error and is used as a tool to guide the repositioning of the tooth.

After completing individual teeth matching, the technician selects done button 78 in the dialog box shown in FIG. 11 to finish the bite matching process. The program will then compare the teeth matching result to a stoppage limit to make sure that the teeth are matched within tolerance and automatically adjust the gingiva and copy the original final setup into the current case setting. In the preferred embodiment of the present disclosure, the limit for all teeth, except the last molars, are set at default 0.1 mm. last molars limit is set at 0.15 mm.

FIG. 15 is a screen shot of a message warning the technician that at least one tooth is over the acceptable matching surface limit, according to one embodiment of the present disclosure. If any teeth are over the acceptable matching surface limit (0.1 mm), a warning message is generated telling the technician to re-match the listed teeth to prevent the creation of unfitted aligners. If the technician attempts to finish a case while there are still teeth over the limit by selecting a 'NO' button 86, the program will prevent the technician from finishing the case by automatically closing the file, after asking the technician to re-cut the case.

It is possible in some cases that the dialog box of FIG. 11 may display a large number of teeth that cannot be matched. For those cases the following steps would be performed until a satisfactory result is obtained:

(1) If the initial matching was checked and was satisfactory, then the parameters of the matching might have been too restrictive for the particular case and it may be necessary to modify the parameters with a greater tolerance and re-run the matching algorithm again;

(2) An impression discrepancy might contribute to the resulting errors. In this case, the technician might decide that the current errors are acceptable and the teeth would actually be in approximately the correct position (or the same position if the case was re-cut on the corrected bite);

(3) Have excess material removed from the starting impression. and start again by executing the rough bite matching algorithm; and (4) Begin the treatment process again as bite matching is not possible.

In one embodiment, since segmentation is not performed on a Current Teeth Image, it reduces time for a mid-course correction.

In another embodiment, the Previously Segmented Teeth Model of a patient's teeth is used to detect deviations from the planned course of treatment which can occur at any stage during the treatment. By adjusting any teeth that are off track in the Previously Segmented Teeth Model, a corrected set of stages can be created. Additional appliances are generated from the corrected set of stages. The additional appliances will reposition the patient's teeth to the preexisting Prescribed Tooth Arrangement or a pre-existing stage so that the remainder of the appliances can be used to obtain the prescribed tooth arrangement.

While the present disclosure is described above with respect to what is currently considered its preferred embodiments, it is to be understood that the disclosure is not limited to that described above. To the contrary, the disclosure is intended to cover various modifications and equivalent arrangements within the spirit and scope of the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for transmitting an adjusted three-dimensional (3D) model of a patient's teeth generated based on a two-dimensional (2D) image of the patient's teeth, the method comprising:
scanning the patient's teeth using a scanning device to obtain a 3D digital model of the patient's teeth;
accessing the 2D image of the patient's teeth, the 2D image based on a camera picture;
iteratively comparing teeth of the 3D digital model to teeth of the 2D image by comparing a distance between corresponding points on one or more teeth of the 3D digital model and of the 2D image, and generating the adjusted 3D model of the patient's teeth in which the one or more teeth of the 3D digital model are moved to reduce said distance, wherein iteratively comparing and generating comprises iterating until one or more deviations between the teeth of the 3D digital model and the 2D image are below a threshold; and
transmitting the adjusted 3D model to an output module for generating an orthodontic treatment plan for realigning the patient's teeth.

2. The method of claim 1, wherein iteratively comparing the teeth of the 3D digital model to the teeth of the 2D image further comprises comparing surfaces of one or more teeth in the 3D digital model with one or more teeth in the 2D image.

3. The method of claim 1, further comprising generating the orthodontic treatment plan for realigning the patient's teeth, wherein the orthodontic treatment plan comprises a reboot plan or a refinement plan.

4. The method of claim 3, wherein generating the orthodontic treatment plan comprises generating at least one corrected stage based on the adjusted 3D model, wherein the corrected stage is based on the adjusted 3D model.

5. The method of claim 1, further comprising pre-processing the 2D image to assign a unique identifier to each tooth for comparison with the 3D digital model.

6. The method of claim 5, wherein the unique identifier comprises a specific characteristic of the respective tooth.

7. The method of claim 5, wherein the unique identifier comprises a Facial Axis of the Clinical Crown (FACC).

8. The method of claim 5, wherein iteratively comparing the teeth of the 3D digital model to the teeth of the 2D image further comprises comparing the unique identifiers assigned to the 2D image to unique identifiers of the 3D digital model.

9. The method of claim 1, wherein the 2D image comprises the camera picture.

10. The method of claim 1, wherein the 2D image is a current teeth image.

11. A method for transmitting an adjusted three-dimensional (3D) model of a patient's teeth generated based on a two-dimensional (2D) image of the patient's teeth, the method comprising:
accessing a 3D digital model of the patient's teeth based on a scan of the patient's teeth;
capturing the 2D image of the patient's teeth with a camera device;
iteratively comparing teeth of the 3D digital model to teeth of the 2D image by comparing a distance between corresponding points on one or more teeth of the 3D digital model and of the 2D image, and generating the adjusted 3D model of the patient's teeth in which the one or more teeth of the 3D digital model are moved to reduce said distance, wherein iteratively comparing and generating comprises iterating until one or more deviations between the teeth of the 3D digital model and the 2D image are below a threshold; and
transmitting the adjusted 3D model to an output module for generating an orthodontic treatment plan for realigning the patient's teeth.

12. The method of claim 11, further comprising iteratively comparing the teeth of the 3D digital model to the teeth of the 2D image by comparing surfaces of one or more teeth in the 3D digital model with one or more teeth in the 2D image.

13. The method of claim 11, further comprising accessing the 3D digital model by accessing a previously segmented teeth model.

14. The method of claim 11, further comprising generating at least one corrected stage based on the adjusted 3D model, wherein the corrected stage is based on the adjusted 3D model.

15. The method of claim 11, further comprising pre-processing the 2D image to assign a unique identifier to each tooth for comparison with the 3D digital model.

16. The method of claim 15, further comprising iteratively comparing the teeth of the 3D digital model to the teeth of the 2D image by comparing the unique identifier.

17. A multi-module system for transmitting an adjusted three-dimensional (3D) model of a patient's teeth generated based on a two-dimensional (2D) image of the patient's teeth, the system comprising:
- a camera device configured to capture the 2D image of the patient's teeth comprising a current teeth image;
- a receive module configured to receive a 3D digital model of the patient's teeth, the 3D digital model having been generated based on a scan of the patient's teeth by a first computing device, and to receive the 2D image of the patient's teeth;
- a compare module and a repositioning module, wherein the compare module is configured to iteratively compare teeth of the 3D digital model to teeth of the 2D image by comparing a distance between corresponding points on one or more teeth of the 3D digital model and of the 2D image, and the repositioning module is configured to generate the adjusted 3D model of the patient's teeth in which the one or more teeth of the 3D digital model are moved to reduce said distance, wherein iteratively comparing and generating comprises iterating until one or more deviations between the teeth of the 3D digital model and the 2D image are below a threshold; and
- an output module configured to transmit the adjusted 3D model for generating an orthodontic treatment plan for realigning the patient's teeth.

18. The multi-module system of claim 17, wherein the compare module is configured to iteratively compare the 3D digital model to the 2D image by comparing surfaces of one or more teeth between the 3D digital model and the 2D image.

19. The multi-module system of claim 17, wherein the output module is configured to generate at least one corrective stage based on the adjusted 3D model.

20. The multi-module system of claim 17, wherein the receive module, the compare module, the repositioning module and the output module are part of a network.

21. The multi-module system of claim 17, further comprising an analysis module configured to pre-process the 2D image to assign a unique identifier for comparison with the 3D digital model.

22. The multi-module system of claim 21, wherein the compare module is configured to iteratively compare the teeth of the 3D digital model to the teeth of the 2D image of the patient's teeth by comparing the unique identifiers.

23. A method for receiving an adjusted three-dimensional (3D) model of a patient's teeth generated based on a two-dimensional (2D) image of the patient's teeth, the method comprising:
- scanning the patient's teeth using an intraoral scanning device to obtain a 3D digital model of the patient's teeth;
- providing, to a computing system, the 3D digital model of the patient's teeth wherein the computing system is configured to:
  - iteratively compare teeth of the 3D digital model to teeth of the 2D image of the patient's teeth by comparing a distance between corresponding points on one or more teeth in the 3D digital model and in the 2D image, and generate the adjusted 3D model of the patient's teeth in which the one or more teeth in the 3D digital model are moved to reduce said distance, wherein iteratively comparing and generating comprises iterating until one or more deviations between the teeth of the 3D digital model and the 2D image are below a threshold; and
- receiving, from the computing system, the adjusted 3D model.

24. The method of claim 23, further comprising generating an orthodontic treatment plan for realigning the patient's teeth, wherein the orthodontic treatment plan comprises a reboot plan or a refinement plan.

25. The method of claim 23, further comprising pre-processing the 2D image to assign a unique identifier to each tooth for comparison with the 3D digital model, wherein the unique identifier comprises a specific characteristic of the respective tooth.

26. The method of claim 23, further comprising generating at least one corrected stage based on the adjusted 3D model.

* * * * *